United States Patent
Tedeschi et al.

(10) Patent No.: US 6,645,518 B2
(45) Date of Patent: Nov. 11, 2003

(54) USES FOR MEDICAL DEVICES HAVING A LUBRICIOUS, NITRIC OXIDE-RELEASING COATING

(76) Inventors: Eugene Tedeschi, 3053 Porter Creek Rd., Santa Rosa, CA (US) 95404; Chirag B. Shah, 71 Achilles Way, North Attleboro, MA (US) 02763

( * ) Notice: Subject to any disclaimer, the term of this patent is extended or adjusted under 35 U.S.C. 154(b) by 0 days.

(21) Appl. No.: 10/137,236

(22) Filed: Apr. 30, 2002

(65) Prior Publication Data

US 2002/0122814 A1 Sep. 5, 2002

Related U.S. Application Data

(63) Continuation of application No. 09/726,856, filed on Nov. 30, 2000, now Pat. No. 6,379,691, which is a continuation-in-part of application No. 09/405,024, filed on Sep. 27, 1999, now Pat. No. 6,218,016, which is a continuation-in-part of application No. 09/163,038, filed on Sep. 29, 1998, now Pat. No. 6,299,980.

(51) Int. Cl.$^7$ .......................... A61F 2/00; A61F 13/00; A61K 31/74

(52) U.S. Cl. .................... 424/423; 424/422; 424/78.08; 514/824

(58) Field of Search ................................ 424/423, 422, 424/78.08; 514/824

(56) References Cited

U.S. PATENT DOCUMENTS

| | | |
|---|---|---|
| 3,632,557 A | 1/1972 | Brode et al. |
| 4,373,009 A | 2/1983 | Winn |
| 4,585,666 A | 4/1986 | Lambert |
| 4,625,012 A | 11/1986 | Rizk et al. |
| 5,032,666 A | 7/1991 | Hu et al. |
| 5,040,544 A | 8/1991 | Lessar et al. |
| 5,134,192 A | 7/1992 | Feijen et al. |
| 5,405,919 A | 4/1995 | Keefer et al. |
| 5,470,307 A | 11/1995 | Lindall |
| 5,512,055 A | 4/1996 | Domb et al. |
| 5,525,348 A | 6/1996 | Whitbourne et al. |
| 5,525,357 A | 6/1996 | Keefer et al. |
| 5,605,696 A | 2/1997 | Eury et al. |
| 5,612,052 A | 3/1997 | Shalaby |
| 5,645,931 A | 7/1997 | Fan et al. |
| 5,662,960 A | 9/1997 | Hostettler et al. |
| 5,674,192 A | 10/1997 | Sahatjian et al. |
| 5,676,963 A | 10/1997 | Keefer et al. |
| 5,698,738 A | 12/1997 | Garfield et al. |
| 5,718,892 A | 2/1998 | Keefer et al. |
| 5,770,229 A | 6/1998 | Tanihara et al. |
| 5,770,645 A | 6/1998 | Stamler et al. |
| 5,776,611 A | 7/1998 | Elton et al. |
| 5,797,887 A | 8/1998 | Rosen et al. |
| 5,849,368 A | 12/1998 | Hostettler et al. |
| 5,919,570 A | 7/1999 | Hostettler et al. |
| 6,379,691 B1 * | 4/2002 | Tedeschi et al. ............ 424/423 |

FOREIGN PATENT DOCUMENTS

| | | |
|---|---|---|
| EP | 0352295 | 1/1990 |
| EP | 0357401 | 3/1990 |
| EP | 0397784 | 11/1990 |

OTHER PUBLICATIONS

Bernard Lambermont, Vincent D'Orio, Philippe Kolh, Paul Gerard, Roland Marcelle; *Effects of Inhaled Nitric Oxide on Pulmonary Hemodynamics in a Porcine Model of Endotoxin Shock;* Critical Care Medicine, Sep. 1999 vol. 27, No. 9, pp. 1953–1957.

R. Holopainen, H. Aho, J. Laine, P. Kappa; *Nitric Oxide Inhalation Inhibits Pulmonary Apoptosis but not Inflammatory Injury in Porcine Meconium Aspiration;* An International Journal of Paediatrics, vol. 88/Oct. 1999/No. 10, pp. 1147–1155.

John W. Berkenbosch, Davinia E. Withington; *Management of Postoperative Chylothorax with Nitric Oxide: A Case Report;* Critical Care Medicine, vol. 27 No. 5, May 1999, pp. 1022–1024.

Karina Lewis, Alain Cadieux, Giles A. Rae, Jean–Philippe Gratton, Pedro D'Orleans–Juste; *Nitric Acid Limits the Eicosanoid–Dependant Bronchoconstriction and Hypotension Induced ByEndothelin–1 in the Guinea Pig;* British Journal of Pharmacology, Jan. 1999, vol. 126(1), pp. 93–102.

Acta Neurochirurgica; The European Journal of Neurosurgery, vol. 141 No. 12, 1999.

T. Kiris, A. Karasu, C. Yavuz, T. Erdem, F. Unal, K. Hepgul and H. Baloglu; *Reversal of Cerebral Vasospasm by the Nitric Oxide Donor SNAP in an Experimental Model of Subarachnoid Haemorrhage;* Acta Neurochirurgica, The European Journal of Neurosurgery, vol. 141 No. 12 1999.

Robert R. Freedman, Reda Girgis, Maureen D. Mayes; *Acute Effect of Nitric Oxide Raynaud's Phenomenon in Scleroderma;* The Lancet, vol. 354, No. 9180, Published Aug. 28, 1999.

(List continued on next page.)

*Primary Examiner*—Thurman K. Page
*Assistant Examiner*—Blessing Fubara
(74) *Attorney, Agent, or Firm*—Louis C. Cullman

(57) ABSTRACT

Methods are provided for delivering nitric oxide to the vascular tissue of a patient to inhibit or prevent restenosis or improve vascular function following various surgical procedures or associated with various NO-related conditions. The disclosed methods comprise contacting the vascular tissue of a patient with a medical device coated with a coating comprising nitric oxide associated with and releaseable from a polyurea network formed from the reaction on said medical device of a polyisocyanate; an amine donor and/or hydroxyl donor; an isocyanatosilane adduct having terminal isocyanate groups and at least one hydrolyzable alkoxy group bonded to silicon; and optionally a polymer selected from the group consisting of polyethylene oxide, polyvinyl pyrrolidone, polyvinyl alcohol, polyethylene glycol, and polyacrylic acid.

5 Claims, No Drawings

OTHER PUBLICATIONS

Michael Carrier, Gilbert Blaise, Sylvain Belisle, Louis Perrault, Michel Pellerin, Robert Petitclerc, L. Conrad Pelletier; *Nitric Oxide Inhalation in the Treatment of Primary Graft Failure.*
*Following Heart Transplantation*; The Journal of Heart and Lung Transplantation, vol. 18, No. 7, Jul. 1999.

Kevin J. Sullivan, Salvatore R. Goodwin, Jennifer Evangelist, Robert D. Moore, Paulette Mehta; *Nitric Oxide Successfully used to treat Acute Chest Syndrome of Sickle Cell Disease in a Young Adolescent;* Critical Care Medicine, vol. 27, No. 11 (Nov. 1999).

Catherine E. Adams, Karen E. Stevens; *Inhibition of Nitric Oxide Synthase Disrupts Inhibitory Gating of Auditory Responses in Rat Hippocampus;* The Journal of Pharmacology and Experimental Therapeutics, vol. 287 No. 2, pp. 760–765.

Andrea M. Cooper, Brahm H. Segal, Anthony A . Frank, Steven M. Holland, Ian M. Orme; *Transient Loss of Resistance to Pulmonary tuberculosis in p47PHOX–/–Mice;* Infection & Immunity, Mar. 2000, vol. 68, No. 3, pp. 1231–1234.

Satoshi Ishihara, John A. Ward, Osamu Tasaki, Basil A. Pruitt Jr, Cleon W. Goodwin Jr, David W. Mozingo, William G. Cioffi Jr; *Inhaled Nitric Oxide Prevents Left Ventricular Impairment during Endotoxemia;* Journal of Applied Physiology, Dec. 1998, vol. 85, No. 6, pp. 2018–2024.

Brian R. Jacobs, Richard J. Brilli, Edgar T. Ballard, Daniel J. Passerini; Daniel J. Smith; *Aerosolized Soluble Nitric Oxide Donor Improves Oxygenation and Pulmonary Hypertension in Acute Lung Injury;* Respiratory and Critical Care Medicine, vol. 158, No. 5, Nov. 1998, pp. 1536–1542.

T. Murphy Goodwin, Robert B. Gherman, Afshan Hameed and Uri Elkayam; *Favorable Response of Eisenmenger Syndrome to Inhaled Nitric Oxide during Pregnancy;* American Journal of Obstetrics and Gynecology, Jan. 1999, vol. 180, No. 1, pp. 64–67.

Brigitte Samama, Nelly Boehm; *Inhibition of Nitric Oxide Synthase Impairs Early Olfactory Associative Learning in Newborn Rats;* Neurobiology of Learning and Memory, vol. 71, No. 2, (Mar. 1999), pp. 219–231.

Mostafa A. El–Haddad, Conrad R. Chao, Sheng–Xing Ma, Michael G. Ross; *Nitric Oxide Modulates Spontaneous Swallowing Behavior in Near–Term Ovine Fetus;* American Journal of Physiology, vol. 277, No. 4, Oct. 1999, pp. R981–R986.

R. Gradini, M. Realacci, A. Ginepri, G. Naso, C. Santangelo, O. Cela, P. Sale, A. Berardi, E. Petrangeli, M. Gallucci, F. Di Silverio, M.A. Russo; *Nitric Oxide Synthases in Normal and Benign Hyperplastic Human Prostate: Immunohistochemistry and molecular biology;* The Journal of Pathology, 189 pp. 224–229 (1999).

Didier Payen, Jane Muret, Sadek Beloucif, Claire Gatecel, Nathalie Kermarrec, Nathalie Guinard, Joaquim Mateo; *Inhaled Nitric Oxide, Almitrine Infusion, or Their Coadministration as a Treatman of Severe Hypoxemic Focal Lung Lesions;* Anesthesiology, Nov. 1998, vol. 89, No. 5, pp. 1157–1165.

* cited by examiner

USES FOR MEDICAL DEVICES HAVING A LUBRICIOUS, NITRIC OXIDE-RELEASING COATING

This application is a continuation of Ser. No. 09/726,856 filed Nov. 30, 2000 now U.S. Pat. No. 6,379,691, which is a continuation-in-part of U.S. application Ser. No. 09/405,024, filed Sep. 27, 1999, is now U.S. Pat. No. 6,218,016, which is a continuation-in-part of U.S. application Ser. No. 09/163,038, filed Sep. 29, 1998 is now U.S. Pat. No. 6,299,980 which applications are herein incorporated by reference in their entirety.

BACKGROUND OF THE INVENTION

1. Field of the Invention

This invention relates generally to the uses for a drug-coating complex which is drug-releasing in physiological media. More particularly, the invention relates to methods of using medical devices coated with a lubricious, nitric oxide-releasing coating for the treatment of vascular disorders, including restenosis, and the induction of angiogenesis.

2. Related Art

It has long been known that hydrophilic coatings with low friction (coefficient of friction of 0.3 or less) are useful for a variety of medical devices such as catheters, catheter introducers and the like. When low friction surfaces are used, the devices, upon introduction into the body, slide easily within arteries, veins and other body orifices and passageways. There have been a wide variety of methods used to provide the surfaces desired. In some cases the material of the catheter or medical device is formed of a material having good anti-friction properties such as poly(tetrafluoroethylene) or other plastics which tend to avoid abrasion with the body. However, in many cases the selection of materials does not provide the anti-slip properties desired in conjunction with other desirable properties for the particular medical device.

Prior art hydrophilic coatings typically rely on a two step, two coating process, usually involving a primer coat of isocyanate or isocyanate/polymer blend which is dried, followed by a second coat containing at least one hydrophilic polymer such as polyvinyl pyrrolidone or polyethylene oxide. The two coatings, one superimposed on the other, are then baked to effect a cure. This forms an interpolymer complex or a network including the hydrophilic polymer. Several disadvantages to this process exist.

First, the exact ratio of primer material to the hydrophilic polymer is difficult to control, as it depends on whatever amounts of primer and hydrophilic polymer happen to be deposited by the wet film during the respective coating steps. Second, the primer may begin to redissolve in the second coating solution, causing some loss of primer and further resulting in difficulty in controlling the primer/hydrophilic polymer ratio. Third, the hydrophilic polymer is not covalently bonded to the substrate and may bond to other materials in the area leading the coating to lose its desired properties. Fourth, additional facilities and time are needed for coating with a two step process, as compared to a one step process.

Prior patents have suggested applying solutions of polyvinylpyrrolidone with isocyanate and/or polyurethane in multi-step operations. These coatings often lack good durability. For example, U.S. Pat. No. 4,585,666 issued to Lambert discloses medical devices having hydrophilic coatings formed from an isocyanate layer overcoated with a polyvinylpyrrolidone layer. However, the multistep procedure makes it difficult to tailor the properties and values of the final coatings.

U.S. Pat. No. 4,625,012, Rizk et al., describes a one step method for preparing moisture curable polyurethane polymers having pendant alkoxysilane groups and isocyanate terminals on a substrate. The method includes reacting an isocyanatosilane adduct and an isocyanate different from the isocyanatosilane with a polyol. The isocyanatosilane adduct and the isocyanate have at least two isocyanato groups each. Furthermore, the isocyanatosilane is produced by reacting an isocyanate having at least three isocyanato groups with an organofunctional alkoxysilane. The coating formed, however, is not lubricious.

In U.S. Pat. No. 4,373,009, Winn, a coating process for preparing a lubricious coating is disclosed. A coupling agent is first applied to the substrate. A coating is then applied on top of the coupling agent. The coupling agent bonds the coating to the substrate. Although the coupling agent and coating may be applied to the substrate from the same solution, the preferred method is to apply them separately.

U.S. Pat. No. 5,645,931, Fan et al., describes a one step coating process for preparing a thromboresistant lubricious coating. The coating is comprised of a substantially homogeneous composite of polyethylene oxide and polyisocyanate in an inert solvent. However, the one step coating process is only suitable for polymeric substrates.

U.S. Pat. No. 5,662,960, Hostettler et al., describes a process for producing slippery, tenaciously adhering hydrogel coatings containing a polyurethane-polyurea (PU/PUR) hydrogel commingled with a poly(N-vinyl pyrolidone) hydrogel. The coating may be applied on plastic, rubber, or metallic substrates. However, the process is performed in several steps. Initially, plastic substrates are activated by oxidative chemical treatments and plasma treatments with oxygen or nitrogen containing plasma gases. Metallic substrates are treated with aminosilane primers. Then, a base coat of PU/PUR hydrogel is applied to the substrate followed by the application of a coat of a second hydrogel.

Exposure to a medical device which is implanted or inserted into the body of a patient can cause the body tissue to exhibit adverse physiological reactions. For instance, the insertion or implantation of certain catheters or stents can lead to the formation of emboli or clots in blood vessels. Similarly, the implantation of urinary catheters can cause infections, particularly in the urinary tract. Other adverse reactions to medical devices include inflammation and cell proliferation which can lead to hyperplasia, occlusion of blood vessels, platelet aggregation, rejection of artificial organs, and calcification.

To counter the adverse reactions which often accompany a medical implant or insert, pharmaceutically-active agents have been applied to or embedded within medical devices by covering the surface with a coating containing the active agent. Accordingly, medical device coatings are known which release a pharmaceutically-active agent via dissolution of the active agent or by cleavage of the active agent from the coating. Other drug-releasing coatings operate by hydrolyzing or otherwise cleaving a coating-active agent bond.

One approach to the incorporation of a pharmaceutically active agent into a polymeric network is to absorb the active agent into the coating from a solution. Hydrophilic polymers in contact with an aqueous solution of an active agent, such as by soaking the polymer in a solution of the active agent, will swell to contain the solution and absorb the active agent dissolved therein. Upon drying, the polymeric network includes the associated active agent. The use of such a polymeric network as a coating for a medical device allows for the association and immobilization of a water soluble active agent with and/or within the medical device. The active agent can then be released from the coating upon contact with aqueous body fluids.

Another approach to the association of a pharmaceutically-active agent with a polymeric coating is by chemical attachment, e.g., covalent attachment, of the active agent to the coating. For example, coating compositions are known which include a nitric oxide-releasing functional group bound to a polymer. U.S. Pat. Nos. 5,676,963 and 5,525,357 disclose such polymeric coating compositions.

Nitric oxide (NO), has been implicated in a variety of bioregulatory processes, including normal physiological control of blood pressure, macrophage-induced cytostasis and cytotoxicity, and neurotransmission. NO inhibits the aggregation of platelets. NO also reduces smooth muscle cell proliferation thereby reducing restenosis. Consequently, NO can be used to prevent and/or treat complications such as restenosis and thrombus formation when delivered to treatment sites inside an individual that have come in contact with medical devices.

Several hypotheses regarding the mechanism of action of NO in various processes have been put forward but none has yet been proven conclusively. These hypotheses include such disparate ideas as 1) NO may stop cellular proliferation and induce a program of differentiation (Babaei et al. *Circ. Res.* 82:1007–1015 (1998)) and/or 2) that there are dual signals required for NO to be active, e.g. that NO induces scalar motion in cells but that a second signal, possibly provided by a growth factor, is needed to indicate the direction in which motion will occur (Noiri et al. *Am. J. Physiol.* 274:C236–C244 (1998)). Other investigators have reported that ribonucleotide reductase is inhibited by NO, explaining the cell-cycle specific effect of NO in inhibiting vascular smooth muscle cell proliferation (Sarkar et al. *J. Hypertens.* 15:275–283 (1997)). Because NO is such a potent, multifaceted biological response modifier, the challenge in the development of NO-based pharmaceuticals is to deliver an effective amount locally.

Restenosis limits the successful outcome of percutaneous procedures used to recanalize atherosclerotic coronary arteries. Ischemic heart disease caused by atherosclerotic lesions of coronary arteries underlies about 500,000 to 600,000 deaths per year (Bierman, E. L., *Atherosclerosis and Other Forms of Arteriosclerosis* in Principles of Internal Medicine, Braunwald, E. et al. Eds., McGraw-Hill, New York, (1987)). Current surgical therapies used to circumvent these lesions include coronary artery bypass graft surgery (CABG) and less invasive procedures such as percutaneous translumenal coronary angioplasty (PTCA) or atherectomy. PTCA is performed in approximately 400,000 US patients and 650,000 patients world-wide (Lemaitre et al *Angioplasty Industry—Slower Growth on Tap as Balloon Prices Deflate*, Cowen-Industry Strategies, Cowen & Co., 1–70 (1994)). The major problem associated with PTCA is the occurrence of restenosis (late arterial narrowing) which occurs in about 30–40 percent of all patients undergoing PTCA (Blackshear et al. *J. Am. Coll. Cardiol.* 9:834–848 (1987)) within 3–6 months.

The pathophysiology of restenosis is complex but localized. Injury to the arterial wall during angioplasty is the initiating event causing restenosis, but progression and severity are influenced by extent of vascular injury and platelet aggregation, individual anatomic and hemodynamic conditions, disruption of the endothelial lining and stimulation of vascular smooth muscle cell proliferation, migration, and extracellular matrix secretion (Bauters et al. *Cardiovasc. Res.* 31:835–846 (1996); Landzberg et al. *Progr. Cardiovasc. Diseases* XXXIX:361–398 (1997)).

Improved therapies for restenosis are needed. Only a small number of therapies are currently approved for human use. Surgical approaches in addition to repeat angioplasty include CABG or the less invasive procedure of directional atherectomy. These procedures are more expensive, more traumatic, and therefore less preferred except in unusual circumstances. The only FDA-approved pharmacologic agent for use after balloon angioplasty is administration of the potent anti-platelet agent, GPIIb/IIIa antibody (c7E3), which inhibits thrombus formation and acute reclosure, and has recently been reported to reduce clinical restenosis by 20–30 percent at six month follow-up (Gottsauner-Wolf et al. *Clin. Cardiol.* (*USA*) 19:347–356 (1996)). However, its utility remains limited by the fact that (i) it is administered systemically and, unless heparin dose is carefully controlled, it can lead to bleeding complications; (ii) it is only effective in 20–30 percent of cases; and (iii) its high price has limited its widespread use for all angioplasty patients (Holmes, D. R. *N. Engl. J. Med.* 336:1748–1749 (1997)).

Mechanical approaches, used in ca. 25 percent of angioplasty procedures performed in 1995, include two types of FDA-approved intracoronary stents, the Gianturco-Roubin Flex-Stent (Cook Cardiology) and the Palmaz-Schatz stent (Johnson & Johnson). Recently, two other coronary stents were approved for use in the U.S., the Medtronic/AVE XT Stent, with its unique "rib-cage" design, and Bard's MEMOTHERM®, a Nitinol self-expanding stent, is now used throughout the world. Stents are endovascular metal alloy scaffoldings of 10–20 mm in length, which, when inserted after angioplasty, produce an initially larger coronary lumen and prevent vessel recoil. Stents limit the long-term build-up of plaque and scar tissue, reducing clinical restenosis by 20–30% after 6 months, but are still subject to late reclosure due to smooth muscle cell overgrowth and thrombus formation (Bauters et al. *Cardiovasc. Res.* 31:835–846 (1996); Gottsauner-Wolf et al. *Clin. Cardiol.* (*USA*) 19:347–356 (1996)).

Loss of endothelial NO after arterial injury may contribute to restenosis. NO is one of at least three locally vasoactive systems, the other two being angiotensin II and bradykinin (Gibbons, S. H. *Clin. Cardiol.* 20(Supp2):II–II1835 (1997)). Under basal conditions, NO modulates vascular tone, serves as an antithrombotic agent, and inhibits vascular smooth muscle cell proliferation. Deficiency of this critical biological modifier may contribute to a variety of vascular disorders, including hypertension, atherosclerosis and restenosis (Myers et al. Int. *J. Cardiol.* 55:183–191 (1996)). Replacement of this endogenous level of NO may prove therapeutic for these conditions. Unfortunately, short therapeutic half-life, drug tolerance and systemic absorption with potentially adverse hemodynamic effects limit the use of conventional nitrate preparations.

Myocardial ischemia (reduction in blood flow and/or oxygen supply) occurs in a variety of clinically important settings, ranging from coronary artery disease and stable angina to myocardial infarction. The present invention addresses these problems by restoring the heart's blood supply. In the case of vessel blockage, successful removal of that blockage may be reversed by restenosis. Prevention of restenosis is essential.

Replacement of NO reduces restenosis. Other methods of NO replacement have been tried such as gene therapy; in fact, direct transfer of a cDNA encoding endothelial NO synthase has been shown to inhibit neointimal lesion formation and improve vascular reactivity (von der Leyden et al. *Semin. Interv. Cardiol.* 1:209–214 (1996)). Although exciting, such gene transfers are costly and relatively inefficient. Creation of a local depot of an NO-generating agent capable of sustained NO release is an attractive alternative.

Of interest are the NCI group's studies on the effect of NO release rate on the growth of vascular smooth muscle cells in vitro (Mooradian et al. *J. Cardiovascular Pharmacol.* 25:674–678 (1995)). Three N-nitroso compounds with radically different half lives were evaluated: SPER/NO ($t_{1/2}$ of 39 minutes); DPTA/NO ($t_{1/2}$ of 3 h) and DETA/NO ($t_{1/2}$ of 20 h). An inverse relationship was found between the $IC_{50}$ values and the half lives, suggesting that this type of NO donor would also prove to be useful inhibitors of intimal hyperplasia and restenosis after vascular injury.

Induced angiogenesis can be therapeutic and may be mediated by NO. Therapeutic angiogenesis results from the induction of new blood vessel development in areas with limited blood flow (Engler, D. A., *Circulation* 94:1496–1498 (1996); Simons, M. and Ware, J. A., *Nature Med.* 2:519–520 (1996)). Isner's group (Murohara et al., *J. Clin. Invest.* 101:2567–2578 (1988)) tested the hypothesis that endothelial NO synthase, and thus NO, modulates angiogenesis in rabbits and mice with operatively induced hindlimb ischemia and concluded that NO synthase modulates angiogenesis in response to tissue ischemia.

NO can stimulate angiogenesis in combination with transmyocardial laser revascularization. Transmyocardial laser revascularization improves heart function and quality of life in patients with refractory coronary ischemic syndromes (Mirhoseini et al., *Ann. Thorac. Surg.* 45:415–420 (1988); Donovan et al., *Am. Coll. Cardiol.* 30:607–612 (1997); Horvath et al., *J. Thorac. Cardiovasc. Surg.* 113:645–653 (1997); Cooley et al., *J. Thorac. Cardiovasc. Surg.* 111:791–797 (1996); Horvath et al., *J. Thorac. Cardiovasc. Surg.* 111:1047–1053 (1996)). The mechanism of laser revascularization does not depend on long term patency of myocardial channels but more likely stimulation of angiogenesis (Yamamoto et al., *J. Am. Coll. Cardiol.* 31:1426 (1998); Gassler et al., *Circulation* 95:371–375 (1997); Kohmoto et al., *Ann. Thorac. Surg.* 61(3):861–868 (1996); Burkhoff et al., *Ann. Thorac. Surg.* 61(5):1532–1534 (1996)). Approaches to increase regional blood flow via direct delivery of angiogenic factors or their cognate genes have also demonstrated promise and numerous clinical trials have begun (Yanagisawa-Miwa et al., *Science* 257:1401–1403 (1992); Giordano et al., *Nat. Med.* 2:534–539 (1996); Mack et al., *J. Thorac. Cardiovasc. Surg.* 115:168–176 (1998); Baumgartner et al., *Circulation* 97:1114–1123 (1998); Lazarous et al., *Circulation* 94:1074–1082 (1996); Schumacher et al., *Circulation* 97:645–650 (1998); Laham et al., *J. Am. Col. Cardiol.* 31(supp. A):394A (1998); Henry et al., *J. Am. Col. Cardiol.* 31(supp. A):65A (1998)).

The best characterized angiogenic factors, VEGF and bFGF, are also NO-dependent vasodilators (Horowitz et al, *Arterioscler Thromb. Vasc. Biol.* 17:2793–2800 (1997)). Myocardial ischemia upregulates VEGF, its receptors and NO release (Kitakaze et al., *J. Mol. Cell. Cardiol.* 27:2149–2154 (1995); Node et al., *Circulation* 93:356–364 (1996)) and blocking endogenous NO production inhibits VEGF induced angiogenesis (Ziche et al., *J. Clin. Invest.* 99:2625–2634 (1997), Hood et al., Am. *J. Physiol* 274:H1054–H1058 (1998)). Myocardial implant devices stimulate angiogenesis and provide a logical platform for delivering therapeutic factors to augment the heart's angiogenic response. NO is a potent vasodilator and mediator of angiogenesis. An NO-generating implant device would therefore be expected to represent a safer, more efficacious and less costly approach for treating patients with refractory coronary ischemic syndromes' (so-called "no option" patients) and mediating the induction of angiogenesis.

The systemic benefits of NO treatment are known. Inhaled NO is a modulator of distal pulmonary tone in endotoxin-induced pulmonary hypertension (Lambermont et al, *Crit. Care Med.* 27(9):1953–1957 (1999)), implicating NO as an agent for improving pulmonary circulation. The effects of NO inhalation on pulmonary hypertension and blood flow has been demonstrated in combination with other hemodynamic agents (prostacyclin, Max et al., *Intensive Care Med.* 25(10):1147–1154 (1999)); and (almitrine, Paven et al., *Anesthesiology* 89(5):1157–1165 (1998)).

Other recognized or implicated systemic benefits of NO therapy include: the treatment of benign prostatic hyperplasia (Gradini et al., *J. Pathol.* 189(2):224–229 (1999)); the regulation of amniotic fluid (El-Haddad et al., *Am. J. Physiol.* 277 (4 Pt2):R981–R986 (1999)); the stimulation of olfactory associative learning (Samama et al., *Neurobiol. Learn. Mem.* 71(2):219–231 (1999)); the correction of hypoxemia associated with Eisenmenger syndrome (Goodwin et al., *Am. J. Obstet. Gynecol.* 180(1 Pt 1):64–67 (1999)); the prevention of the impairment of left ventricle contractility after endotoxemia (Ishihara et al., *J. Appl. Physiol.* 85(6):2018–2024 (1998)); the treatment of ventilation/perfusion mismatch and pulmonary hypertension associated with acute respiratory distress syndrome (Jacobs et al., *Am. J. Respir. Crit. Care Med.* 158(5 Pt 1):1536–1542 (1998)); the mediation of sensory inhibition (Adams et al., *J. Pharmacol. Exp. Ther.* 287(2):760–765 (1998)); the control of Mycobacterium tuberculosis during primary pulmonary infection (Cooper et al., *Infect. Immun.* 68(3): 1231–1234 (2000)); the treatment of acute chest syndrome of sickle cell disease (Sullivan et al., *Crit. Care Med.* 27(11):2563–2568 (1999)); the treatment of Raynard's phenomenon in scleroderma patients (Freedman et al., *Lancet* 354(9180):739 (1999)); the improvement of cardiac function after heart transplantation (Carrier et al., *J. Heart Lung Transplant* 18(7):664–667 (1999)); the maintenance of cerebrovascular tone and the reversal of cerebral vasospasms (Kiris et al., *Acta Neurochir (Wien)* 141(12):1323–1328, 1328–1329 (1999)); the improvement of pulmonary and systemic circulation after endothelial induced bronchoconstriction (Lewis et al., *Br. J. Pharmacol.* 126(1):93–102 (1999); the reduction of chest tube drainage and decrease of pulmonary artery pressure (Berkenbosch et al., *Crit. Care Med.* 27(5):1022–1024 (1999)); and the control of pulmonary artery pressure, the improvement in arterial oxygenation efficiency and the prevention of epethelial apoptosis (Holopainen et al., *Acta Paediatr.* 88(10):1147–1155 (1999)).

Nitric oxide appears to also play a primary role in the development of an erection and the controllable and predictable release of NO to the penis by a catheter or other delivery means coated with or made of a NO-releasing polymer is described in U.S. Pat. No. 5,910,316.

Because nitric oxide, in its pure form, is a highly reactive gas having limited solubility in aqueous media, it is difficult to introduce in a reliable and controllable form. NO is too reactive to be used without some means of stabilizing the molecule until it reaches the treatment site. Thus, NO is generally delivered to treatment sites in an individual by means of polymers and small molecules which release NO.

In mammalian cells, NO arises through the action of a family of NO synthases which catalyze the oxidation of one of the two guanidino nitrogens in L-arginine. NO is made by a variety of cells including vascular endothelial cells and platelets. Because it is a potent biological regulator, NO also can induce cell killing and/or hypotension. For this reason its administration must be closely controlled. Implant devices made from materials coupled to NO-generating agents should address the need to deliver an effective amount of NO locally without the introduction of toxic, free radical effects.

Different approaches to providing pharmacologically active NO have been tried. It is known that long-term oral administration of the NO precursor, L-arginine, enhances NO production and reduces restenosis (McNamara et al. BBRC 193:291–296 (1993)). Local intramural delivery of L-arginine is also effective in rabbits (Schwarzacher et al. Circulation 95:1863–1869 (1997)), restoring endothelium-dependent vasodilation and enhancing local NO production. Chronic inhalation of NO inhibits neointimal formation in the rat (Lee et al. Circ. Res. 78:337–342 (1996)) but would be difficult clinically. Interestingly, treatment of 700 stable coronary patients by local infusion of the NO-donor linsidomine followed by oral molsidomine (another NO-donor) over a 6 month period was associated with only a modest improvement in the long-term angiographic result but had no effect on clinical outcome (the ACCORD study; Lablanche et al. Circulation 7:83–89 (1997)), supporting the idea that NO is best given locally at higher concentrations than are possible systemically because of the multitude of potential side effects of systemic administration. Support for this method of administration has been provided by Loscalzo's group (Marks et al. J. Clin. Invest. 96:2630–2638 (1995)) who demonstrated inhibition of neointimal proliferation in rabbits after vascular injury by a single local treatment with S-nitroso serum albumin, a naturally occurring adduct of NO. Stents coated with this protein also significantly reduce restenosis.

The present invention is directed to overcoming the shortcomings of current NO therapy by combining the benefits of a lubricious coating with the therapeutic and prophylactic benefits associated with an NO-releasing coating, and using such coated medical devices to treat vascular conditions, including restenosis, and induce angiogenesis.

SUMMARY OF THE INVENTION

One aspect of the present invention is directed to a coated substrate comprising (a) a substrate; and (b) a polyurea and/or polyurethane network capable of accommodating a pharmaceutically-active agent, said polyurea and/or polyurethane network formed from the reaction, on at least a portion of the surface of said substrate to be coated, of a mixture comprising a polyisocyanate; an amine donor and/or a hydroxyl donor; an isocyanatosilane adduct having at least one terminal isocyanate group and at least one hydrolyzable alkoxy group bonded to silicon; and optionally a polymer selected from the group consisting of polyethylene oxide, polyvinyl pyrrolidone, polyvinyl alcohol, polyethylene glycol, and polyacrylic acid.

It is a further aspect of the present invention to provide an article comprising a substrate on which a coating is formed comprising a polyurea and/or polyurethane network capable of accommodating a pharmaceutically-active agent, formed from the reaction, on a substrate to be coated, of a mixture comprising a polyisocyanate; an amine donor and/or a hydroxyl donor; an isocyanatosilane adduct having terminal isocyanate groups and at least one hydrolyzable alkoxy group bonded to silicon; and optionally, a polymer selected from the group consisting of polyethylene oxide, polyvinyl pyrrolidone, polyvinyl alcohol, polyethylene glycol, and polyacrylic acid; in a solvent.

It is a further aspect of the present invention to provide a drug-releasing coating comprising an active agent associated with and releaseable from a polymeric network formed from the reaction, on a substrate to be coated, of a mixture comprising a polyisocyanate; an amine donor; and an isocyanatosilane adduct having terminal isocyanate groups and at least one hydrolyzable alkoxy group bonded to silicon; and optionally, a hydroxyl donor and/or a polymer selected from the group consisting of polyethylene oxide, polyvinyl pyrrolidone, polyvinyl alcohol, polyethylene glycol, and polyacrylic acid; in a solvent.

According to yet another aspect of the present invention, a method is provided of preparing a lubricious coating on a substrate to be coated comprising: forming a mixture of a polyisocyanate, an amine donor and/or a hydroxyl donor; a polymer selected from the group consisting of polyethylene oxide, polyvinyl pyrrolidone, polyvinyl alcohol, polyethylene glycol, and polyacrylic acid; and an isocyanatosilane adduct having terminal isocyanate groups and at least one hydrolyzable alkoxy group bonded to silicon, in a solvent; applying the mixture to the substrate; and curing the mixture on the substrate to form the coating.

A further aspect of the present invention is to provide a method of preparing a nitric oxide-releasing coating on a substrate to be coated, comprising: forming a mixture of a polyisocyanate, an amine donor, an isocyanatosilane adduct having terminal isocyanate groups and at least one hydrolyzable alkoxy group bonded to silicon, and optionally a hydroxyl donor and/or a polymer selected from the group consisting of polyethylene oxide, polyvinyl pyrrolidone, polyvinyl alcohol, polyethylene glycol, and polyacrylic acid, in a solvent; applying the mixture to the substrate; contacting the coated substrate with a nitric oxide-releasing agent; and curing the mixture on the substrate to form the coating.

It is a further aspect of the present invention to provide a nitric oxide-releasing coated article or medical device produced by or produceable by the coating method of the present invention.

It is a further aspect of the present invention to provide methods of delivering a therapeutic dose of nitric oxide in a patient in need thereof by contacting the vascular tissue of a patient with a medical device coated with a lubricious, nitric oxide-releasing coating of the invention.

These and other features and objects of the invention are more fully appreciated from the following detailed description of preferred embodiments of the invention.

DETAILED DESCRIPTION OF THE PREFERRED EMBODIMENTS

According to the present invention, a lubricious coating is formed by the reaction, on a substrate to be coated, of a mixture comprising a polyisocyanate; an amine donor and/or a hydroxyl donor; an isocyanatosilane adduct having terminal isocyanate groups and at least one hydrolyzable alkoxy group bonded to silicon; and a polymer selected from the group consisting of polyethylene oxide, polyvinyl pyrrolidone, polyvinyl alcohol, polyethylene glycol, and polyacrylic acid; in a solvent. The resulting coating is drug-accommodating and, when the optional hydrophilic polymer is incorporated into the mixture, becomes highly lubricious.

It is believed that the isocyanate functional groups of the polyisocyanate and isocyanatosilane react with the amine donor to form a polyurea network or with the hydroxyl donor to form a polyurethane network. Furthermore, the silane groups of the isocyanatosilane are believed to form covalent bonds with the substrate to which the coating is applied when cured in the presence of moisture to form a strongly adherent coating.

The coating mixture is prepared in solution by weighing the appropriate quantities of polyisocyanate; amine donor and/or hydroxyl donor; isocyanatosilane adduct; and a polymer selected from the group consisting of polyethylene oxide, polyvinyl pyrrolidone, polyvinyl alcohol, polyethylene glycol, and polyacrylic acid; and adding them into an appropriate mixing vessel. Additional solvents may be added to adjust the viscosity of the mixture. The choice of ingredients in the coating mixture also affects the physical properties of the overall coating. Solids contents in a range of from about 0.2 to about 2.5% are preferred. This solution is mixed well and then applied to an appropriate substrate such as catheter tubes, medical tubing introducers, polymer coated medical wires, stents, dilatation balloons, implants, prostheses, and penile inserts, by conventional coating application methods. Such methods include, but are not limited to, dipping, spraying, wiping, painting, solvent swelling, and the like.

The materials of construction of a suitable substrate include, but are not limited to, polymers, metal, glass, ceramics, composites, and multilayer laminates of the aforementioned materials.

The coatings of the present invention are drug-accommodating. As used herein, the term "drug accommodating" refers to the ability of the polymeric network of the coating to associate with a pharmaceutically active agent. The association of the polymeric network of the coating with a pharmaceutically active agent may be accomplished by any mode of molecular recognition or inclusion including, but not limited to, ionic interactions, hydrogen bonding and other dipole—dipole interactions, covalent attachment, interpenetration by solvent swelling, metal ion-ligand interactions, hydrophilic interactions, hydrophobic interactions including π-π stacking interactions, or any combination thereof.

The terms "pharmaceutically active agent", "biologically active compound", "active agent" and "drug" are used herein interchangeably and include pharmacologically active substances that produce a local or systemic effect in an animal. The terms thus mean any substance intended for use in the diagnosis, cure, mitigation, treatment or prevention of disease or in the enhancement of desirable physical or mental development and conditions in an animal. The term "animal" used herein is taken to include humans, sheep, horses, cattle, pigs, dogs, cats, rats, mice; birds; reptiles; fish; insects; arachnids; protists (e.g. protozoa); and prokaryotic bacteria.

The active agents that can be delivered according to the present invention include inorganic and organic drugs without limitation and include drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autocoid systems, alimentary and excretory systems, histamine systems, and the like. The active drug that can be delivered for acting on these recipients includes, but is not limited to, anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids sympathomimetics, parasympathomimetics, tranquilizers, urinary tract drugs, vaccines, vaginal drugs, vitamins, collagen, hyaluronic acid, nonsteroidal anti-inflammatory drugs, angiotensin converting enzymes, polynucleotides, polypeptides, polysaccharides, and the like.

The present invention is particularly suitable for delivering polypeptide drugs which are water soluble. Exemplary drugs include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors; interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; and peptide or polypeptide vaccines. Other particularly suitable drugs include polysaccharide including, but not limited to, hyaluronic acid.

Preferred drugs include anti-thrombogenics, such as heparin and heparin complexes, enoxaprin, aspirin and hirudin; anti-proliferatives, such as monoclonal antibodies capable of blocking smooth muscle cell proliferation, heparin, angiopeptin and enoxaprin; and antioxidants, such as nitric oxide. Preferred heparin complexes include, but are not limited to, heparin-tridodecylmethylammonium chloride, heparin-benzalkonium chloride, heparin-steralkonium chloride, heparin-poly-N-vinyl-pyrrolidone, heparin-lecithin, heparin-didodecyldimethylammonium bromide, heparin-pyridinium chloride, and heparin-synthetic glycolipid complex.

A preferred embodiment of the present invention involves contacting a medical device having a lubricious, drug-accommodating, coating of the invention with an aqueous solution containing a pharmaceutically active agent dissolved or dispersed therein. A hydrophilic polymer coating, or other cellular polymeric coating, when exposed to a solution of an active agent, such as an aqueous solution of heparin, will swell to contain the solution. Upon drying and/or vacuum removal of the solvent, what is left behind is a coated substrate surface which contains the active agent (e.g., heparin) in an inwardly decreasing concentration gradient of an interpenetrating polymeric network. The resulting coating becomes drug releasing when exposed to, and consequently re-hydrated or at least partially dissolved with, aqueous biological fluids.

Another preferred embodiment of the present invention is directed to contacting a medical device having a drug-accommodating coating of the invention with a pharmaceutically active agent capable of forming a covalent bond with one or more functional groups within the polymeric network, such that the pharmaceutically-active agent becomes bound to the coating. In a most preferred embodiment, the nucleophilic nitrogen atoms of the polyurea network are allowed to react with an organic or inorganic compound to form a covalent bond. The resulting coating-active agent bond preferably cleaves to release the active agent when used on a medical device in an environment which can cleave the bond. For example, for covalent bonds subject to cleavage by hydrolysis, the coating becomes drug-releasing in an aqueous environment. For enzymatically-cleavable bonds, the coating becomes drug-releasing in the presence of a suitable enzyme.

An especially preferred active agent for association or bonding to the drug-accommodating coating of the present invention is nitric oxide (NO). Physical association or bonding of an $N_2O_2$ or $N_2O_2^-$ functional group to the polymeric network may be achieved by covalent attachment of a nucleophilic moiety of the polymeric coating with $N_2O_2$. The nucleophilic residue to which the $N_2O_2$ or $N_2O_2^-$ group is attached may form part of the polymer itself, i.e., part of the polymer backbone, or may be attached as pendant groups on the polymer backbone. The manner in which the $N_2O_2$ or $N_2O_2^-$ functional group is associated, part of, or incorporated with or contained within, i.e., "bound," to the polymer is inconsequential to the present invention and all means of association, incorporation and bonding are contemplated herein. For example, the $N_2O_2$ or $N_2O_2^-$ functional groups of the present invention can be coupled to reactive amine groups to form diazeniumdiolates using methods such as those disclosed in U.S. Pat. Nos. 5,039,705, 5,366,997, and 5,405,919, the entire contents of which are hereby incorporated by reference.

The NO-releasing $N_2O_2$ or $N_2O_2^-$ functional group is preferably a nitric oxide/nucleophile adduct, e.g., the reaction product of nitric oxide and a nucleophile. The nucleophilic residue is preferably that of a primary amine, a secondary amine, a polyamine or derivatives thereof. Most preferably, the nucleophilic adduct is a urea derivative, such as the polyurea network formed by the reaction of the amine donor with the polyisocyanate and/or isocyanatosilane of the coating composition.

The nitric oxide-releasing $N_2O_2$ or $N_2O_2^-$ functional groups that are bound to the polymer generally are capable of releasing nitric oxide in an aqueous environment such as body fluid, i.e., they do not require activation through redox or electron transfer. While the polymer-bound NO-releasing coating compositions of the present invention are capable of releasing NO in an aqueous solution, such a composition preferably releases NO under physiological conditions.

After applying the coating solution to a substrate, the solvent is preferably allowed to evaporate from the coated substrate, such as by exposure to ambient conditions for at least 5 minutes.

The coating is subsequently cured. The cure time, temperature, and humidity vary with the choice of solvent, polyisocyanate; polyol and polyamine; isocyanatosilane adduct; and the composition of the substrate. The curing rate may be increased by the addition of small amounts water to the coating mixture prior to applying the coating to the substrate.

Cure temperatures may range from about 75° F. to about 350° F. Cure times may range from about 2 minutes to about 72 hours, depending upon the solvent, cure temperature and the reactivity of the polyisocyanate, amine donor, and isocyanatosilane adduct. Preferred cure conditions are about 150° F. to about 220° F. for about 20 minutes to about 8 hours. In all cases the cure conditions should be non-deleterious to the underlying substrate.

After the coating is cured, it is preferable to rinse or soak the coating in water to remove any uncomplexed polymers. Generally, a brief rinse of 10–15 seconds is sufficient, however, a longer rinse or soak is acceptable since the coating is cured and forms a stable gel when in contact with water. After rinsing, the coating may be dried either at ambient conditions, or at elevated temperatures or combinations thereof at reduced pressure.

After the coating is formed, the coating can imbibe water from an aqueous solution prior to introduction to the body and can become lubricious. Alternatively, the coating can imbibe water solely from body fluids, even if not exposed to water prior to introduction into the body. Because the coating is a cross-linked system, it adheres well to the substrate even when hydrated. The coating retains its lubricating properties even after subsequent drying and rehydration. If the coating is to be used in a body-related application, such as in catheters, introducer tubes and the like, the materials selected should be compatible with the body and non-toxic to the body. Biocompatible materials include, but are not limited to, polyethylene, polypropylene, polyurethane, naturally occurring polymers, stainless steel and other alloys.

The coating may be applied to various substrates, including, but not limited to, metals, ceramics, polymers, and glass.

The coating may be applied to metal substrates such as the stainless steel used for guide wires, stents, catheters and other devices.

Organic substrates which may be coated with the coatings of this invention include, but are not limited to, polyether block amide, polyethylene terephthalate, polyetherurethane, polyesterurethane, other polyurethanes, natural rubber, rubber latex, synthetic rubbers, polyester-polyether copolymers, polycarbonates, and other organic materials. Some of these materials are available under various trademarks such as Pebax™ available from Atochem, Inc. of Glen Rock, N. J.; Mylar™ available from E.I. duPont deNemours and Co. of Wilmington, Del.; Texin™ 985A from Bayer Corporation of Pittsburgh, Pa.; Pellethane™ available from Dow Chemical of Midland, Mich.; and Lexan™ available from General Electric Company of Pittsfield, Mass.

The polyisocyanate is preferably an aromatic polyisocyanate. More preferably, the polyisocyanate is an aromatic polyisocyanate based on toluene diisocyanate and is dissolved in propylene glycol monomethyl acetate and xylene. Preferably, the amount of polyisocyanate ranges from about 0.2 to about 10 percent by weight based upon 100% total weight of coating mixture. Particularly preferred polyisocyanates include m-xylylene diisocyanate, m-tetramethylxylylene diisocyanate known as meta-TMXDI available from Cytec Industries, Inc., Stamford, Conn., and the aromatic polyisocyanate known as Desmodur CB 60N available from Bayer Corporation, Pittsburgh, Pa.

Examples of suitable amine donors which may be incorporated in the mixture in addition to or in lieu of a hydroxyl donor include, but are not limited to, $C_1$–$C_{10}$ cycloalkyl, alkyl and alkenyl monoamines such as methylamine, ethylamine, diethylamide, ethylmethylamine, triethylamine, n-propylamine, allylamine, isopropylamine, n-butylamine, n-butylmethylamine, n-amylamine, n-hexylamine, 2-ethylhexylamine, cyclohexylamine, ethylenediamine, polyethyleneamine, 1,4-butanediamine, 1,6-hexanediamine, N-methylcyclohexylamine and alkylene amines such as ethyleneimine. Preferred amine donors include triethylene glycolamine which has the formula $H_2NCH_2CH_2OCH_2CH_2OCH_2CH_2NH_2$ and an approximate molecular weight of about 148 available as Jeffamine™ XTJ-504 from Huntsman Corp., Salt Lake City, Utah; polyetherdiamines such as Jeffamine™ XTJ-500 and XTJ-501 which have a predominantly polyethylene oxide backbone and an approximate molecular weight of 600 and 900, respectively, available from Huntsman Corp., Salt Lake City, Utah; polyethertriamines such as Jeffamine™ T-403 which is a polypropylene oxide-based triamine and has an approximate molecular weight of 440 available from Huntsman Corp., Salt Lake City, Utah; and amine terminated polypropyleneglycols such as Jeffamine™ D-400 and Jeffamine™ D-2000 which have approximate molecular weights of 400 and 2000, respectively. Other amine donors include urethane modified melamine polyols containing amine and hydroxyl groups available as Cylink HPC™ from Lytec Industries, West Patterson, N.J.

The hydroxyl donor is preferably a polyol. Polyols useful in this invention may be any of a large number of polyols reactive with the polyisocyanate and isocyanatosilane to form a polyurethane network. Examples of suitable polyols include, but are not limited to, polyester polyols, polyether polyols, modified polyether polyols, polyester ether polyols, castor oil polyols, and polyacrylate polyols, including Desmophen™ A450, A365, and A160 available from Bayer Corporation, Pittsburgh, Pa. Preferred polyols include castor oil derivatives (triglyceride of 12-hydroxyoleic acid) such as DB oil, Polycin™ 12, Polycin™ 55, and Polycin™ 99F available from CasChem, Inc. of Bayonne, N.J. More preferably, the polyol is polyester based, such as Desmophen™ 1800. Suitable diols include, but are not limited to, poly(ethylene adipates), poly(ethyleneglycol adipates), polycaprolactone diols, and polycaprolactone-polyadipate copolymer diols, poly(ethyleneterephthalate) polyols, polycarbonate diols, polytetramethylene ether glycol, ethyleneoxide adducts of polypropylene triols. Suitable products include Desmophen™ 651A-65, 1300–75 and 800 available from Bayer Corporation of Pittsburgh, Pa., Niax™ E-59 and others available from Union Carbide of Danbury, Conn., Desmophen™ 550DU, 1600U, 1920D, and 1150 available from Bayer Corporation. Many other polyols are available and may be used as known to those skilled in the art.

Coating solutions containing amine donors are typically easier to process, quicker to cure, and form more rigid, lower viscosity coatings than coating solutions containing hydroxyl donor and no amine donor. Coating solutions containing amine donors, however, typically have a shorter pot life and form less flexible coatings than coating solutions containing hydroxyl donors.

Hydroxyl donors in the coating solution cause the formation of polyurethane. In contrast, amine donors in the coating solution cause formation of a polyurea network. A polyurea network may provide better biocompatibility and stability than a polyurethane network since chain cleavage does not occur. Further, polyurea networks typically have better network properties, such as fatigue resistance, than polyurethane networks.

The amount of hydroxyl and amine donor in the coating mixture may be varied to obtain desirable surface properties for the coating. For example, the amine donor may be varied to obtain a desired lubricity. Preferably, the amount of hydroxyl donor ranges from about 0.2 to about 10 percent by weight and the amount of amine donor ranges from about 0.2 to about 10 percent by weight based upon 100% total weight of coating mixture.

Preferably, the polymer selected from the group consisting of polyethylene oxide, polyvinyl pyrrolidone, polyvinyl alcohol, polyethylene glycol, and polyacrylic acid is polyethylene oxide. More, preferably, the polymer is polyethylene oxide having a molecular weight of about 300,000, such as Polyox™ available from Union Carbide Corp of South Charleston, W. Va. The polymer preferably has a mean molecular weight of from about 100,000 to about 2,000,000. Preferably, the amount of the polymer ranges from about 0.2 to about 20 percent by weight based upon 100% total weight of coating mixture. Reduction of the concentration of the water soluble polymer in the coating matrix will increase the amine concentration in the polymer, thereby increasing the number of nucleophilic amine sites available for reaction with a pharmaceutically-active agent, e.g., by nitrosylation with $N_2O_2$.

The isocyanatosilane adduct has one or more unreacted isocyanate functional groups. An isocyanatosilane having two or more unreacted isocyanate functional groups may be produced by reacting a silane, such as aminosilane or mercaptosilane, with polyisocyanate. The isocyanatosilane has at least one hydrolyzeable alkoxy bonded to silicon. Preferably, the amount of isocyanatosilane ranges from about 0.1 to about 10 percent by weight based upon 100% total weight of coating mixture.

The solvent should not react with the polyisocyanate; amine donor; hydroxy donor; polymer selected from the group consisting of polyethylene oxide, polyvinyl pyrrolidone, polyvinyl alcohol, polyethylene glycol, and polyacrylic acid; or isocyanatosilane adduct but is a solvent for all the components of the mixture. The solvent is preferably free of reactive amine, hydroxyl and carboxyl groups. Suitable solvents include, but are not limited to, methylene chloride, tetrahydrofuran (THF), acetonitrile, chloroform, dichloroethane, dichloroethylene, and methylene bromide. Preferably, the solvent is acetonitrile and THF, especially with a ratio of acetonitrile to THF of about 3:1.

Wetting agents may be added to the coating solution to improve wettability to hydrophobic surfaces. Wetting agents include, but are not limited to, fluorinated alkyl esters, such as Fluorad™ FC-430 available from 3M Corp., and octylphenol ethylene oxide condensates, such as Triton™ X-100 available from Union Carbide. A preferred concentration of wetting agent in the coating solution is from about 0.01 to about 0.2% by weight based upon 100% solids in the coating solution.

Viscosity and flow control agents may be added to the coating mixture to adjust the viscosity and thixotropy of the mixture to a desired level. Preferably, the viscosity is such that the coating may be formed on the substrate at the desired thickness. Viscosities of from about 50 cps to about 500 cps may be used although higher or lower viscosities may be useful in certain instances. Viscosity control agents include, but are not limited to, fumed silica, cellulose acetate butyrate, and ethyl acrylate/2-ethyl hexyl acrylate copolymer. Flow control agents are preferably present in amounts of from about 0.05 to about 5 percent by weight based upon 100% total weight of coating mixture.

Antioxidants may be added to the coating mixture to improve oxidative stability of the cured coatings. Antioxidants include, but are not limited to, tris(3,5-di-t-butyl-4-hydroxybenzyl)isocyanurate, 2,2'-methylenebis(4-methyl- 6-t-butylphenol), 1,3,5-trimethyl-2,4,6-tris(3,5-di-t-butyl-4-hydroxybenzyl)benzene, butylhydroxytoluene, octadecyl 3,5-di-t-butyl-4-hydroxyhydrocinnamate, 4,4 methylenebis (2,6-di-butylphenol), p,p'-dioctyl diphenylamine, and 1,1,3-tris-(2-methyl-4-hydroxy-5-t-butylphenyl)butane. Antioxidants are preferably present in amounts from 0.01 to 1 percent by weight based upon 100% total weight of coating mixture.

Conventional pigments may be added to the coating mixture to impart color or radiopacity, or to improve the appearance of the coatings.

Air release agents or defoamers which are optionally included in the coating solution include, but are not limited to, polydimethyl siloxanes, 2,4,7,9-tetramethyl-5-decyn-4,7-diol, 2-ethylhexyl alcohol, and n-beta-aminoethyl-gamma-amino-propyl-trimethoxysilane. Air release agents are preferably added in amounts from 0.005 to 0.5 percent by weight based upon 100% total weight of coating mixture.

Methods of Use

The present invention provides a method of regulating or modulating a local or systemic biological process or state involving nitric oxide by contacting the tissue of a patient in need thereof with a medical device having a lubricious, nitric oxide-releasing coating of the invention. These biological processes include, but are not limited to, control of blood pressure, macrophage-induced cytostasis and cytotoxicity, neurotransmission, smooth muscle cell proliferation, pulmonary tone, pulmonary and systemic circulation, regulation of amniotic fluid, stimulation of learning processes, mediation of sensory inhibition, cerebrovascular tone, chest tube drainage, and arterial oxygenation.

In one embodiment, a medical device coated with a lubricious, nitric oxide-releasing coating of the invention is used in a method of reducing restenosis or treating or preventing complications associated with restenosis. Persons in need of such treatment and/or prevention include those who have undergone or are undergoing angioplasty, or have experienced a vascular injury. The use of a medical device with a lubricious, nitric-oxide-releasing coating of the invention need not necessarily completely ameliorate restenosis. Further such use can be in conjunction with other treatments for restenosis known to those of skill in the art.

In another embodiment, a medical device coated with a lubricious, nitric-oxide coating of the invention is provided as a "preventive" treatment before detection of restenosis, so as to prevent the same from developing in patients at high risk for the same, such as, for example, angioplasty patients. In particular, a coated medical device of the present invention is used in a method of preventing or reducing restenosis associated with a percutaneous procedure or surgical therapy selected from coronary artery bypass graft surgery (CABG), percutaneous translumenal coronary angioplasty (PTCA), directional atherectomy, and heart transplantation.

In another embodiment, a medical device coated with a lubricious, nitric-oxide-releasing coating of the invention is employed in a method of mediating the induction of angiogenesis. Such a method is useful for inducing new blood vessel development and increasing blood flow in areas with limited blood flow, and particularly useful in patients diagnosed with ischemia. In a preferred embodiment, a device coated with a lubricious, nitric-oxide-releasing coating of the invention is used in combination with transmyocardial laser revascularization to stimulate angiogenesis.

In another embodiment, the present invention is directed to the release of nitric oxide from a medical device coated with a lubricious, nitric-oxide-releasing coating of the invention in a patient that has been diagnosed with a disease or condition which is responsive to NO administration. Diseases or conditions that are treatable according to the present invention include abnormal blood pressure, restenosis, thrombosis, atherosclerosis, hypertension, myocardial ischemic, angina, intimal hyperplasia, benign prostatic hyperplasia, hypoxemia associated with Eisenmenger syndrome, ventilation/perfusion mismatch, acute respiratory distress syndrome, pulmonary infection, acute chest syndrome of sickle cell disease, Raynard's phenomenon in scleroderma patients, and bronchoconstriction.

The patients referred to herein are preferably mammals, and most preferably humans.

Animal Models

In-Stent Restenosis: The porcine stent injury model (Kornowski et al., *J. Am. Coll. Cardiol.* 31:224–230 (1998)) mimics restenosis due to intimal hyperplasia. Coronary vessels are imaged by angiography, injured by inflation of an over-sized balloon catheter, and stents are placed in the injured region by balloon deployment. After 28 days, repeat angiographic images are obtained, the animal is sacrificed and vessels are recovered for determination of restenosis by histomorphometric measures (lumen area, neo-intimal thickness, and % area stenosis). Arterial injury at each stent strut is also quantified for correlation with outcome.

Angiogenesis Induction: The ischemic pig myocardium model and other alternative models of induced, although not therapeutic, angiogenesis are available and can be used to evaluate NO-generating implant materials. The murine angiogenesis model (Passaniti, A., *Lab Invest* 67:804 (1992); Montrucchio et al., *Am. J. Pathol.* 151:557 (1997)) has the advantage of requiring only small samples of materials and providing results within less than one week. In this model, test materials are imbedded in Matrigel, placed in the abdominal wall of mice, and angiogenesis is measured by a blood vessel count in histological sections taken 2–5 days post-implantation.

A pig model of induced angiogenesis can be used for evaluation of NO generating full size myoimplant devices in the appropriate tissue site. In this model four/six metallic implants are placed in the left ventricular wall using a specially designed delivery device. As controls, one hole is cored with a biopsy punch and one additional hole is poked with a needle. During implant placement (or control hole creation), the following measurements are made: systemic blood pressure pre- and post-implant (or control hole); continuous ECG; LV function pre- and post-implant (or control hole); fluoroscopy as needed; and observe time for bleeding to stop, post-implant.

The entire experiment is performed with attention to sterile procedure. After placement of the implants and control holes, the animals are closed, kept alive and blood pressure monitored daily in the first post-operative week.

Upon sacrifice, the hearts are rapidly harvested, perfusion fixed and placed in cold formalin. Coded specimens are photographed, opened along the interventricular septum, X-rayed and implants removed. Tissue surrounding implants from the epicardial and endocardial surface control holes and corresponding untreated areas is embedded in paraffin. LM section (5 microns) are stained with H&E, Masson's trichrome and endothelial cell markers (e.g. anti-vonWillebrand factor and anti-TEK) using standard immunohistochemical techniques.

Slides are evaluated for inflammation (scale of 0–4) and vascular density (number of antibody positive structures with at least one layer of smooth muscle cell/cm$^2$) by a blinded pathologist. Vascular density for the implant regions is compared to the corresponding non-implant regions using a paired student's t-test. Statistical significance is considered a p value <0.05.

Preferably, a successful NO-generating implant will increase vascular density 2-fold compared with the untreated myoimplant. If the NO-generating implant successfully induces angiogenesis in the normal pig myocardium, myoimplants will be tested in a porcine model of ischemic heart disease. This protocol is similar to that described (St. Louis et al., *J. Am. Coll. Cardiol.* 31(*supp. A*):490A (1998)), and is run as outlined below using the same experimental design as for induced angiogenesis in the porcine model.

Chronic Ischemic Pig Model: Mini-swine undergo subtotal left circumflex (LCX) coronary occlusion to reduce resting blood flow to 10% of baseline as assessed using an implanted flow probe (St. Louis et al., *J. Am. Coll. Cardiol.* 31(*supp. A*):490A (1998)). After two weeks in the low-flow state, dubotamine stress echocardiography (DSE) and positron emission tomography (PET) are performed to document ischemic (hibernating) myocardium in the LCX distribution. After verifying ischemia, animals are prepared for myocardial device implants.

PET scans are interpreted as showing ischemic, viable myocardium if a flow deficit is noted in the lateral and posterioinferior walls of the left ventricle supplied by the LCX accompanied by normal or increased glucose utilization in these same regions. Using DSE, viability in the lateral and posterinferior walls of the left ventricle is defined as an improvement in systolic wall thickening with low dose dobutamine in myocardial regions with severe hypocontractility at rest. Viable segments are considered iscehmic if systolic wall motion deteriorates with stress.

The specific variables to be compared are: changes in perfusion by PET 3 months post-implant; changes in wall motion score by DSE 3 months post-implant; time to improvement in wall motion scores by DSE, specifically, performing serial echoes at 1, 2 and 3 months; and vascular density analysis to confirm the presence of endothelial cells within putative neovessels at 3 months.

NO-generating stents are tested according to a modified method described by Kornowski et al., *J. Am. Coll. Cardiol.* 31:224–230 (1998), and outlined below.

Porcine Stent Injury Model: In the porcine stent injury model, pathogen-free domestic pigs are pretreated with aspirin/ticlopidine and slow release verapamil one day before stent placement. Following anesthesia and intubation, heparin is administered I.V. and control angiograms of the left coronary arteries are performed. Before stent implantation, all animals undergo balloon injury for one minute (at 1.2:1 balloon/artery ratio) in the left anterior descending (LAD) and left circumflex (LCX). One stent is balloon-deployed at both sites. Repeat angiograms are obtained immediately after stent implantation. All equipment is removed and the animal is revived and maintained for 28 days under predetermined conditions. Animals undergo repeat angiography in the same orthogonal views before death and perfusion fixed hearts are harvested for histology.

The following Quantitative Coronary Angiographic (QCA) Measurements are made pre- and post-stent implantation and at sacrifice: mean artery reference diameter (proximal and distal); mean stent diameter at full expansion; minimal stent diameter at follow-up; % diameter stenosis at follow-up (mean stent diameter−minimal stent diameter/mean stent diameter×100).

Histomorphometric Analysis: Formalin-fixed specimens are embedded in methacrylate and 50–100 micron sections are obtained at about 1 mm intervals and stained with methylchromatin. Measurements are made on four cross sections from each stent corresponding to the minimal lumen diameter (by QCA) and averaged for each stent: lumen area; neo-intimal thickness; and neo-intimal % area stenosis (1-[stenotic lumen area/original lumen area]×100).

Arterial injury at each stent strut is determined by the anatomic structures penetrated by each strut. Injury score is assigned as: 0, no injury; 1, internal elastic lamina tear; 2, medial tear; and 3, external elastic lamina laceration. The average score for each segment is calculated by dividing the sum of scores by the total number of struts in the examined section.

Dosage/Loading

Defining the loading characteristics of NO-generating molecules onto materials used to create implants and determining the release kinetics under physiological conditions will open the way for the development of many additional types of implant devices. Systemic administration of NO may lead to undesirable side effects because of the large number of processes which are affected by this very powerful biological effector. Local delivery of the molecule from implanted devices represents a very effective way to control both the dose and localization of NO. Accordingly, the determination of the optimal methods for loading NO-generating molecules onto materials suitable for implant construction and the kinetics of release of NO from fully loaded implant materials in buffers and under physiological conditions is an aspect of the present invention.

Loading dosages and release profiles of nitric oxide from a medical device coated with a lubricious, nitric oxide-releasing coating of the invention can be determined readily by those with ordinary skill in the art. Generally, the loading dosage and desired release profile will vary depending upon considerations such as: age; health; medical condition being treated; kind of concurrent treatment, if any; nature of the effect desired; extent of tissue damage; gender; duration of symptoms; and counter indications, if any, and other variables to be adjusted by the individual physician.

An aspect of the present invention is the determination of the maximum amount of each NO-generating molecule which can be loaded onto each type of implant material and the determination of the kinetics of release of NO. As described above, the NO-releasing materials are quantitatively tested for thrombogenicity, an undesirable characteristic, as well as classified as to their cytostatic and angiogenic properties.

The following non-limiting example is meant to be an illustrative embodiment of a lubricious, nitric-oxide releasing coating of the present invention.

EXAMPLE 1

A coating solution was prepared by combining the following ingredients and mixing them thoroughly:

(a) 0.32 g. of an aromatic polyisocyanate adduct based on toluene diisocyanate and dissolved in propylene glycol monomethyl acetate and xylene having an NCO content of about 10.5% and a molecular weight of about 400 available as Desmodur™ CB 60 from Bayer Corporation;

(b) 0.67 g. of a solvent-free, saturated polyester resin (polyol) available as Desmophen™ 1800 from Bayer Corporation;

(c) 0.91 g. of polyethylene oxide available as Polyox™ having a molecular weight of about 300,000 from Union Carbide Corp., (d) 76.97 g. acetonitrile;

(e) 21.82 g. THF; and (f) 2.02 g. 3-isocyanyopropyltriethoxysilane available as UCT 17840-KG from United Chemical Technologies, Bristol, Pa.

Five 18" inch wires were coated with the solution by dipping for 11 seconds. The solvent was evaporated at ambient conditions for approximately 20 minutes. The wires were then placed in an oven at 40° C. for 10 hours to cure the coating.

Upon removal from the oven, the wires were rinsed in water and dried.

The coating was tested by ASTM D 1894–87 Standard Test Methods for Static and Kinetic Coefficients of Friction of Plastic Film and Sheeting.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference in their entirety.

What is claimed is:

1. A method of maintaining cerebrovascular tone within the body of a patient, comprising:

providing a medical device configured to be implanted within the vasculature of a patient;

coating the medical device having a coating comprising:
nitric oxide associated with and releasable from a polyurea network formed from a reaction on the medical device, the reaction comprising a mixture of:

(a) a polyisocyanate;

(b) an amine donor;

(c) an isocyanatosilane adduct having at least one terminal isocyanate group and at least one hydrolyzable alkoxy group bonded to silicon; and optionally (d) a polymer selected from the group consisting of a polyethylene oxide, polyvinyl pyrrolidone, polyvinyl alcohol, polyethylene glycol, and polyacrylic acid; and implanting the coated medical device within the vasculature of the patient.

2. A method of treating the circulatory vasculature of a patient following heart transplantation, comprising:

providing a medical device configured to be implanted within the circulatory vasculature of a patient proximate to the transplanted heart;

coating the medical device having a coating comprising:
nitric oxide associated with and releasable from a polyurea network formed from a reaction on the medical device, the reaction comprising a mixture of:

(a) a polyisocyanate;

(b) an amine donor;

(c) an isocyanatosilane adduct having at least one terminal isocyanate group and at least one hydrolyzable alkoxy group bonded to silicon; and optionally (d) a polymer selected from the group consisting of a polyethylene oxide, polyvinyl pyrrolidone, polyvinyl alcohol, polyethylene glycol, and polyacrylic acid; and implanting within the circulatory vasculature of a patient proximate to the transplanted heart.

3. A method of treating vasospasms within the vasculature of a patient, comprising:

providing a medical device configured to be implanted within the vasculature of a patient;

coating the medical device having a coating comprising:
nitric oxide associated with and releasable from a polyurea network formed from a reaction on the medical device, the reaction comprising a mixture of:

(a) a polyisocyanate;

(b) an amine donor;

(c) an isocyanatosilane adduct having at least one terminal isocyanate group and at least one hydrolyzable alkoxy group bonded to silicon; and optionally (d) a polymer selected from the group consisting of a polyethylene oxide, polyvinyl pyrrolidone, polyvinyl alcohol, polyethylene glycol, and polyacrylic acid; and implanting the coated medical device within the vasculature of a patient.

4. A device for treating the vasculature of a patient, comprising:

a medical device configured to be inserted into the vasculature of the patient; and a coating applied to the medical device, the coating comprising:
nitric oxide associated with and releasable from a polyurea network formed from a reaction on the medical device, the reaction comprising a mixture of:

(a) a polyisocyanate;

(b) an amine donor;

(c) an isocyanatosilane adduct having at least one terminal isocyanate group and at least one hydrolyzable alkoxy group bonded to silicon; and optionally (d) a polymer selected from the group consisting of a polyethylene oxide, polyvinyl pyrrolidone, polyvinyl alcohol, polyethylene glycol, and polyacrylic acid.

5. The device of claim 4 wherein the medical device is selected from the group consisting of catheters, introducer tubes, guidewires, myocardial device implants, and stents.

* * * * *